US012007381B2

(12) United States Patent
Supuren Menguc et al.

(10) Patent No.: US 12,007,381 B2
(45) Date of Patent: Jun. 11, 2024

(54) FABRIC PRICKLE MEASUREMENT TESTER

(71) Applicant: EGE UNIVERSITESI REKTORLUGU, Izmir (TR)

(72) Inventors: Gamze Supuren Menguc, Izmir (TR); Nilgun Ozdil, Izmir (TR)

(73) Assignee: EGE UNIVERSITESI REKTORLUGU, Izmir (TR)

( * ) Notice: Subject to any disclaimer, the term of this patent is extended or adjusted under 35 U.S.C. 154(b) by 420 days.

(21) Appl. No.: 17/434,040

(22) PCT Filed: Feb. 27, 2020

(86) PCT No.: PCT/TR2020/050156
§ 371 (c)(1),
(2) Date: Aug. 26, 2021

(87) PCT Pub. No.: WO2020/176061
PCT Pub. Date: Sep. 3, 2020

(65) Prior Publication Data
US 2022/0120728 A1    Apr. 21, 2022

(30) Foreign Application Priority Data
Feb. 27, 2019  (TR) .................................. 2019/02951

(51) Int. Cl.
*G01N 33/36* (2006.01)
*G01N 19/02* (2006.01)
*G01N 33/00* (2006.01)

(52) U.S. Cl.
CPC .......... *G01N 33/367* (2013.01); *G01N 19/02* (2013.01); *G01N 2033/0086* (2013.01)

(58) Field of Classification Search
CPC ................. G01N 33/367; G01N 19/02; G01N 2033/0086
See application file for complete search history.

(56) References Cited

U.S. PATENT DOCUMENTS

| 5,795,989 | A | * | 8/1998 | Simmons | ............. | G01N 33/367 |
| | | | | | | 73/7 |
| 2012/0213335 | A1 | * | 8/2012 | Chen | .................... | G01N 33/367 |
| | | | | | | 250/307 |
| 2016/0091375 | A1 | * | 3/2016 | Belzacq | ................ | A61F 2/0063 |
| | | | | | | 73/804 |

FOREIGN PATENT DOCUMENTS

| CN | 2679666 Y | 2/2005 |
| CN | 104076133 A | 10/2014 |

(Continued)

OTHER PUBLICATIONS

Donald J Ramsay, et al., An instrument for assessing fabric prickle propensity, Textile Research Journal, 2012, pp. 513-520, 82(5).

(Continued)

*Primary Examiner* — Jamel E Williams
*Assistant Examiner* — Alex T Devito
(74) *Attorney, Agent, or Firm* — Bayramoglu Law Offices LLC

(57) ABSTRACT

A test device for determining the prickle property of the fabrics objectively includes nails on a measuring head fixed in an upper region of the test device, wherein the nails come in the contact with stiff fibers. The test device also includes an operation panel, a light source, a camera, a sample holder. The measurement uses a circular movement of the fabric instead of a linear movement unlike the previous studies. The measuring head does not apply any pressure on the fabric, only by lowering the measurement head, the nails squeezed in the head penetrate in the hairs of the fabric. In this situation, during the movement of the head, prickle force caused by the fiber ends can be detected. With the test device, it is possible to test both woven and knitted fabrics.

1 Claim, 16 Drawing Sheets

(56) References Cited

FOREIGN PATENT DOCUMENTS

| GB | 2285315 | * | 7/1995 | |
| NZ | 593817 A | | 11/2012 | |
| WO | 2010078621 A1 | | 7/2010 | |
| WO | WO-2018050531 A1 | * | 3/2018 | ............. G01N 3/066 |

OTHER PUBLICATIONS

Retrieved from: https://www.woolcomfortandhandle.com/index.php/wool-comfortmeter, Wool Comfort and Handle, 2018.

Maryam Naebe, et al., Associations between the physiological basis of fabric-evoked prickle, fiber and yarn characteristics and the Wool ComfortMeter value, Textile Research Journal, 2015, pp. 1122-1130, vol. 85(11).

D. H. Tester, Relationship between Comfort Meter values and the prickle rating of garments in wearer trials, Animal Production Science, 2010, pp. 1077-1081, 50.

Li-Ming Ao, et al., The Analyzing And Simulating of the Interaction Between Skin and Fabric, Proceedings of the Sixth International Conference on Machine Learning and Cybernetics, 2007, pp. 1154-1558.

Junyan Hu, Characterization of Sensory Comfort of Apparel Products, 2006, The Hong Kong Polytechnic University.

Gamze Süpüren Mengüç, et al., Prickle and handle properties of fabrics produced from specialty animal fibers, Textile Research Journal, 2015, pp. 2155-2167, 85(20).

Prof. Dr.Faruk Bozdoğan, Physical Textile Examinations, 2009, 226 pages.

Gamze Süpüren Mengüç, An Investigation on the Properties of Fabrics Produced from Yarns Spun with Some Specialty Animal Fibers, 2012, 268 pages.

Tiantian Li, et al., The Evaluation of Fabric Prickle Based on BP Neural Network, Advanced Materials Research, 2012, pp. 645-650, vol. 441.

G. R. S. Naylor, et al., Fabric-Evoked Prickle, Textile Research Journal, 1992, pp. 487-493, 62(8).

* cited by examiner

FABRIC PRICKLE MEASUREMENT TESTER

CROSS REFERENCE TO THE RELATED APPLICATIONS

This application is the national phase entry of International Application No. PCT/TR2020/050156, filed on Feb. 27, 2020, which is based upon and claims priority to Turkish Patent Application No. 2019/02951, filed on Feb. 27, 2019, the entire contents of which are incorporated herein by reference.

TECHNICAL FIELD

The present invention is related to various companies that produce yarn, fabric and garments using animal fibers, laboratories that provide analysis services in this sector, consumers, researchers, people having dermatologically sensitive skin and companies that produce textile finishing agents and it is a device that measures fabric prickle objectively.

BACKGROUND

Fabric prickle occurs when the skin is in touch with fabric. Research reveals that the prickle perceived by humans is caused by mechanical impulses affecting the skin surface. These stimuli are caused by fiber ends that come out of the fabric surface and can carry et least 100 mgf without bending and thus affect the pain receptors on the skin surface. (Ao et al., 2007; CSIRO, 1988; Naylor et al., 1992).

If the density of the high-load fiber ends on the fabric surface reaches a certain degree, prickle problem arises. However, to feel fabric prickle, there should be a contact area of more than 5 $cm^2$ between the skin and the fabric. Thus, nerve endings can be stimulated and fabric evoked prickle starts. At this point, the distribution of fiber ends on the fabric surface, bending behaviors, lengths and fineness of fiber ends, the interaction of the skin and the fabric are of great importance. In FIG. 1, the fiber ends indicated with "d" and "e" dent the skin, namely, they cause prickle. However, the fiber indicated by "a" can not dent the skin enough because the length of the fiber end is equal to or less than the contact interspace. When the length of the fiber end is slightly longer than the contact interspace (condition of the fiber b), no prickle occurs because the fiber does not generate enough stimulation in the skin. In some fibers, even if the fiber length is sufficient and remarkably longer than the contact interspace, prickle cannot occur. In this case (the condition of the fiber c), due to the high bending deformations of the fibers (due to the softness of the fibers), it does not create sufficient denting on the skin surface, and no prickle effect occurs (Ao et al., 2007).

Prickle is a fabric property that is evaluated subjectively. In known state of the technique, the prickle of the fabrics is measured by the subjective method, which is defined as "Forearm Method," and is performed by determining the skin irritation by panelists.

In this subjective measurement method performed under standard atmospheric conditions, after the jury member is informed about the test, he/she is placed on a chair and informed about the subjective assessment scale. It is useful to close his/her eyes with a soft fabric in order not to be affected by the fabric appearance. Then, the person who will make the evaluation is asked to put his/her arms on the table with the inside of the arms facing upwards. The test assistant places the fabric, which is chosen randomly, on top of this inner side of the arm. Then, in this region, the fabric is rubbed back and forth with the inside of the arm, people are asked what they feel and are asked to rate the degree of this feeling according to the scale shown at the beginning of the test (Research Center of Hunan Ramie Technology, 1997; Li et al., 2012). However, since the test is subjective, its result is affected by many parameters such as gender, sensitivity and age of the individuals.

When the objective studies conducted in the known state of the technique are examined, it can be seen that the physical properties of the fibers such as diameter, are tried to be determined, in order to estimate the prickle property of the fabrics. However, it affects the reliability of the measurement. Thus, the location of the fiber ends that may cause prickle on the fabric surfaces may differ. While stiff fiber ends having a certain length may dent the skin, it seems that long fiber ends may not.

In the known state of the technique, in the patented measurement device developed by Donald James Ramsay, the fabric surface is scanned after the fabric is placed on the device. During this scan, the fiber ends coming out of the fabric surface pull the wire on the device. Meanwhile, the generated vibration is measured by a sensor. The view of the device is given in FIG. 2. In this device, movement takes place in a linear direction. Since in the device developed by Ramsay (2012) a very large surface is scanned, numerical value of the force is high. Therefore measurement sensitivity can decrease.

In the known state of the technique, Chinese patent document ZL200420019685.6 is about a fabric compression tester and the sensor in the device can detect the pressure applied to the fabric sample. Therefore, in the developed device, the pressure created by the fiber ends on the skin surface can be measured by simulating the interaction between the skin and the fabric. Although, the detail about the area where friction takes place in the device is not given, it is seen that compression takes place in a wide area. Since the number of fibers in the contact area is very high and the resulting force is also expected to be high. In this case, rather than the resistance of the fibers to the compression, a result can be obtained for the measurement of the fabric's compressibility property.

In the device introduced by Ramsay et al. (2012) that is developed at the CSIRO institute in Australia, an objective measurement of fabric prickle was tried to be measured. In the system named as "Wool Comfort Meter", which was developed especially for woolen fabrics, a value defined as the comfort level and expressed in the unit "WCM" is obtained (Wool Comfort and Handle, 2015). It is stated that the device operates according to the principle of counting the fiber ends that cause prickle on the fabric surface. The fabric placed on the platform moves 4 times under the measuring head and the average value of these measurements is calculated. It is stated that the high WCM value given by the device as a result of the measurement increases the risk of the skin irritation caused by fabric (Naebe et al., 2014). Since the designers of the device perform their work using wool fibers in Australia, the device is used for determining the prickle properties of the fabrics produced from wool fibers.

In the "One-side Fabric Compressing Tester" that is described by Ao et al. (2007), the interaction between the skin and the fabric can be measured by measuring the pressure created by the fiber ends on the surface of the fabric. Testing plate links with sensor and surface is covered with latex film to simulate the skin. It perceives the pressure of fabric sample under different distances. The supporting poles are fixed on slider and the slider can move up down with certain speed driven by electrical machinery. As the slider moves up down once, a compressing test is completed. During the compressing testing process (FIG. 3), the test data is collected in accordance with certain collecting density by the data collection system, and the collected "inter-space-pressure" paired data are output to computer applications to carry out necessary processing.

In Fabric Tactile Tester (FTT) device (FIG. 4) which is designed by Hu (2006), thermo-mechanical properties of fabrics can be measured. After the measurements, data related to a total of 17 parameters can be obtained under 4 titles defined as the versatile bending, compression, surface roughness and heat transfer properties of the fabrics. It is explained that the tactile properties such as smoothness, softness, plunge, warmth and humidity are associated with the indices obtained from the FTT device under continuous and non-perceptible sweating conditions (Hu, 2006).

In the known state of the technique, devices developed to determine the fabric prickle property objectively operate according to different principles than the device developed by the invention.

The measuring head of the FricTorq device that is normally used to determine the dynamic friction coefficient (fabric roughness) of the fabrics, was changed and re-designed to measure the fabric prickle instead of kinetic friction coefficient (Supuren Mengüç vd., 2015). The results obtained by using the new head was compared with the results of subjective evaluation and it was proved that this method can be suggested as a new objective method. However there were some measurement constraints that it was not possible to measure all types of textile products and fabrics. The original measuring head of the Frictorq device is 55.65 grams. Although the new designed measurement head is made of low weight material, it was 18.61 grams. Since the measurement head with such a high weight deforms the hairs, the precise measurement of the prickle force is limited.

In the Frictorq device, after the sample is placed on the measurement area, the measuring head is put on the fabric. During the test, by rotating the fabric, the measuring head comes into contact with the sensor located at the top of the instrument and the measurement starts with the increase of the torque. Normally, even during the friction coefficient measurement, depending on the surface properties of the fabric, there may be changes in the position of the measuring head especially in very rough surfaces. The head can change its position from the original insertion point and the measurement stability is negatively affected by this situation. Therefore, this situation adversely affects the accuracy of the test result.

In studies using thin and thick fabrics, different correlation coefficients were determined between objective and subjective measurement results (Supuren Mengüç et al., 2015; Supuren Mengüç, 2012). Therefore, although the loadcell is very sensitive, the need for the measuring head needed to be different for fabrics of different thicknesses and weights. Otherwise, the measuring accuracy in thick fabrics decreased.

Another important point after the measuring head is, inserting fabric sample which will be tested for its prickle property in the sample holder. Sometimes as the thick fabrics are used, it is not possible to close sample holder of Frictorq device. In addition to this, due to its dimensional limitations, the measuring head does not allow measurement.

SUMMARY

The present invention is related to a test device for objective determination of the fabric prickle that meets the above-mentioned requirements, eliminates all the disadvantages, and provides various additional advantages.

The present invention uses a circular movement of the fabric instead of a linear movement unlike the previous studies. During the measurement, simulation of the prickle that will occur as a result of the contact between the skin and the fabric and dynamic friction, and the determination of a physical term, which will be expressed as the "coefficient of prickle" has been provided.

With the invention, stiff, short and thick fibers that cause prickle on fabric surface can be detected with the help of special measurement sensors (heads). When the special designed nails placed on these measurement heads come into contact with stiff fiber ends, a high friction force occurs. Soft fiber ends cannot produce this effect. This effect created by stiff fibers causes a force fluctuation (signal formation) which is determined by the torq sensor.

A databank was created by examining the signals obtained from the measurements using fabrics made from different types of fibers. For this purpose, 70 different types of fabrics were used in this experiment. The fabrics were evaluated by 40 jury members subjectively for their prickle properties. The determined subjective prickle degrees were compared with the results obtained from the developed device. When the results obtained from the different heads developed for woven and knitted fabrics are evaluated in general, it is concluded that the correlation between objective and subjective results is over 80%.

In the device developed by the invention, measurement is conducted by the help of a circular friction force movement, not linear. In this performed movement, the measurement head does not apply any pressure on the fabric, only by lowering the measurement head, the nails squeezed in the head penetrate in the hairs of the fabric. In this situation, during the movement of the head, prickle force caused by the fiber ends can be detected. Therefore, regardless of the thickness of the fabric to be measured, measurements can be conducted.

In the developed invention, a special sample holder was designed, so that it is possible to test all fabric types in different thicknesses and weights from very thin fabrics to coat fabrics.

With the invention, it is possible to test both woven and knitted fabrics.

With this device developed with the invention, thanks to the specially designed sample holder, that makes it possible to test for a wide range of materials, from very fine fabrics of 0.20 mm thickness to diapers of 6 mm thickness or woolen coats of 9 mm thickness.

By means of special equipment used during the development of the device, it is possible to apply different weights on the fabric surface depending on the preferences of the user.

The nails fixed on the measurement head generate vibration due to the bending rigidity of the fibers during the movement. They are very thin having width between 5 mm to 25 mm, and contact only with the hairs on the surface of the fabric. Therefore, a very sensitive measurement can be made. A camera is integrated in the system to control the position of the nails during their penetration in the hairs. The position of the nails can be displayed and recorded during the test.

In addition to the measurement accuracy, another advantage of this instrument is to work with very small test samples providing cost element. The samples that have potential for fabric evoked prickle are mostly wool and special animal fibers which are expensive materials. Therefore, manufacturers or consumers working with these materials do not prefer to work with large samples and to spend too much sample during the test. Considering this expectation in the market, in the developed device, test is conducted with fabric samples having diameter of 90 mm.

Since the measuring head used in this developed device is fixed to the upper part of the device before testing, its weight does not matter. Therefore, more precise measurement of the force fluctuation caused by the protruding fiber ends becomes possible.

DEFINITIONS OF THE PARTS/ASPECTS/SECTIONS FORMING THE INVENTION

1: Operation panel
2: Light Source
3: Camera
4: Sample Holder
5: Measurement Head
6: Thick Fabric Sample
7: Thin Fabric Sample
8: Outer Part of Sample Holder
9: Nonwoven felt
10: Compression Ring
11. Clamping Ring
12. Thin Plate
13. Back of Sample Holder
14. Slot of Sample Holder
15. Nail a: Action of the length of fiber ends is less than or equal to the contact interspace (Previous Technique)
b: Action of the length of fiber ends is slightly longer than the contact interspace (Previous Technique)
c: Action of the length of fiber ends is remarkably longer than the contact interspace (Previous Technique)
d,e: Fiber ends giving sensations of prickle (Previous Technique)

DETAILED DESCRIPTION OF THE EMBODIMENTS

Figure 1:
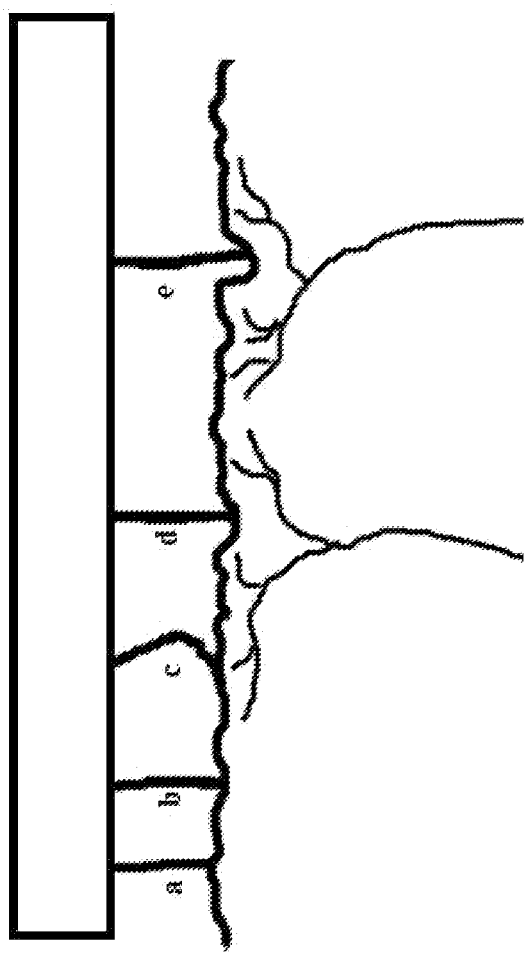
FIG. 1: Effects of different lengths of hairs (Previous Technique) (Ao et al., 2007)
Figure 2:
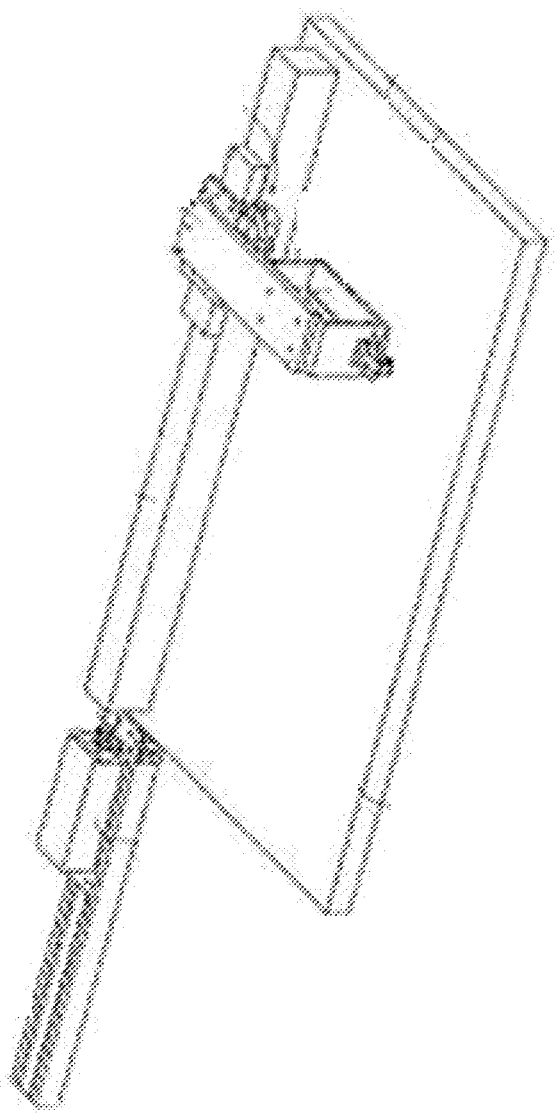
FIG. 2: Technical drawing of the system developed by Donald James Ramsay (James Ramsay Donald, 2012) (Previous technique)
Figure 3:
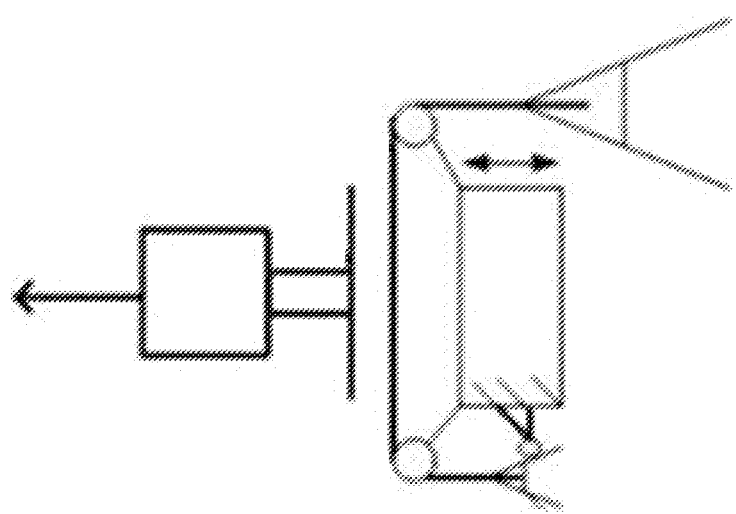
FIG. 3: One-side Fabric Compressing Tester (Ao et al., 2007) (Previous Technique)
Figure 4:
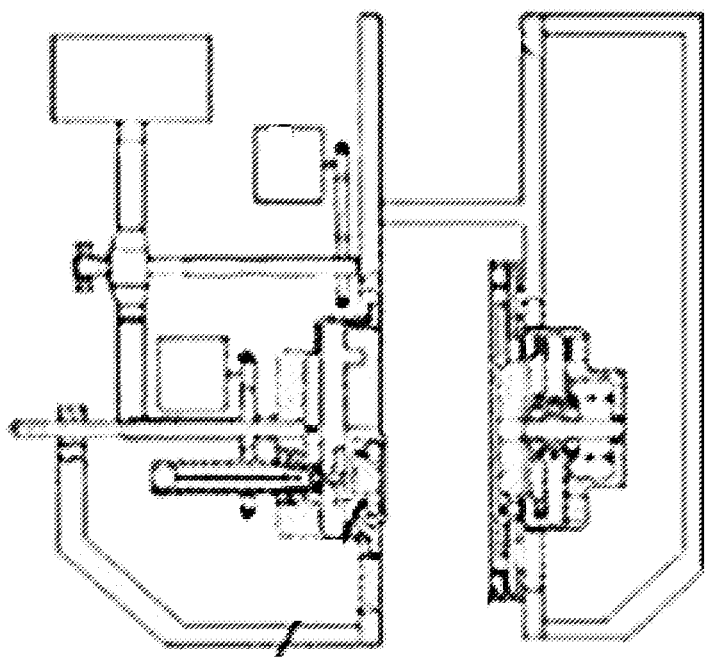
FIG. 4: Schematic view of the Fabric Tactile Tester (FTT) (Previous Technique)
Figure 5:
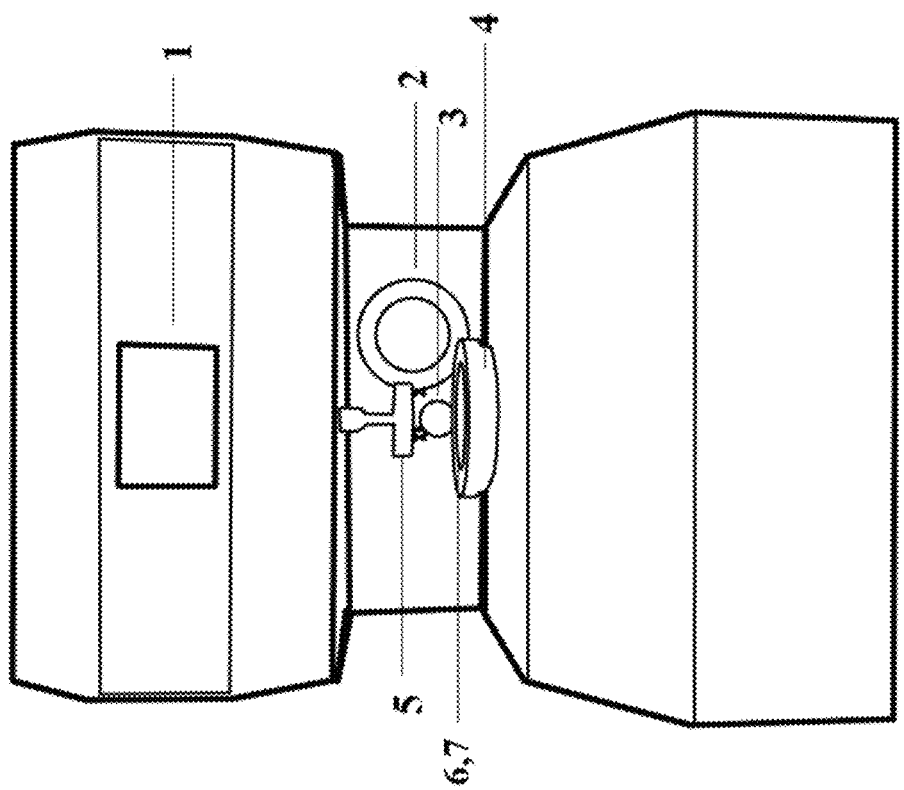
FIG. 5: Fabric Prickle Tester and its sections

The invention is a test device that provides objectively determination of the fabric evoked prickle and consists of 6 basic parts (FIG. 5). These parts are operation panel (1), light source (2), camera (3), sample holder (4), measuring head (5) and sample (6,7). The device measures the moment due to the force created by the fibers causing prickle my means of the nails with a width of 5-25 mm.

Figure 9:
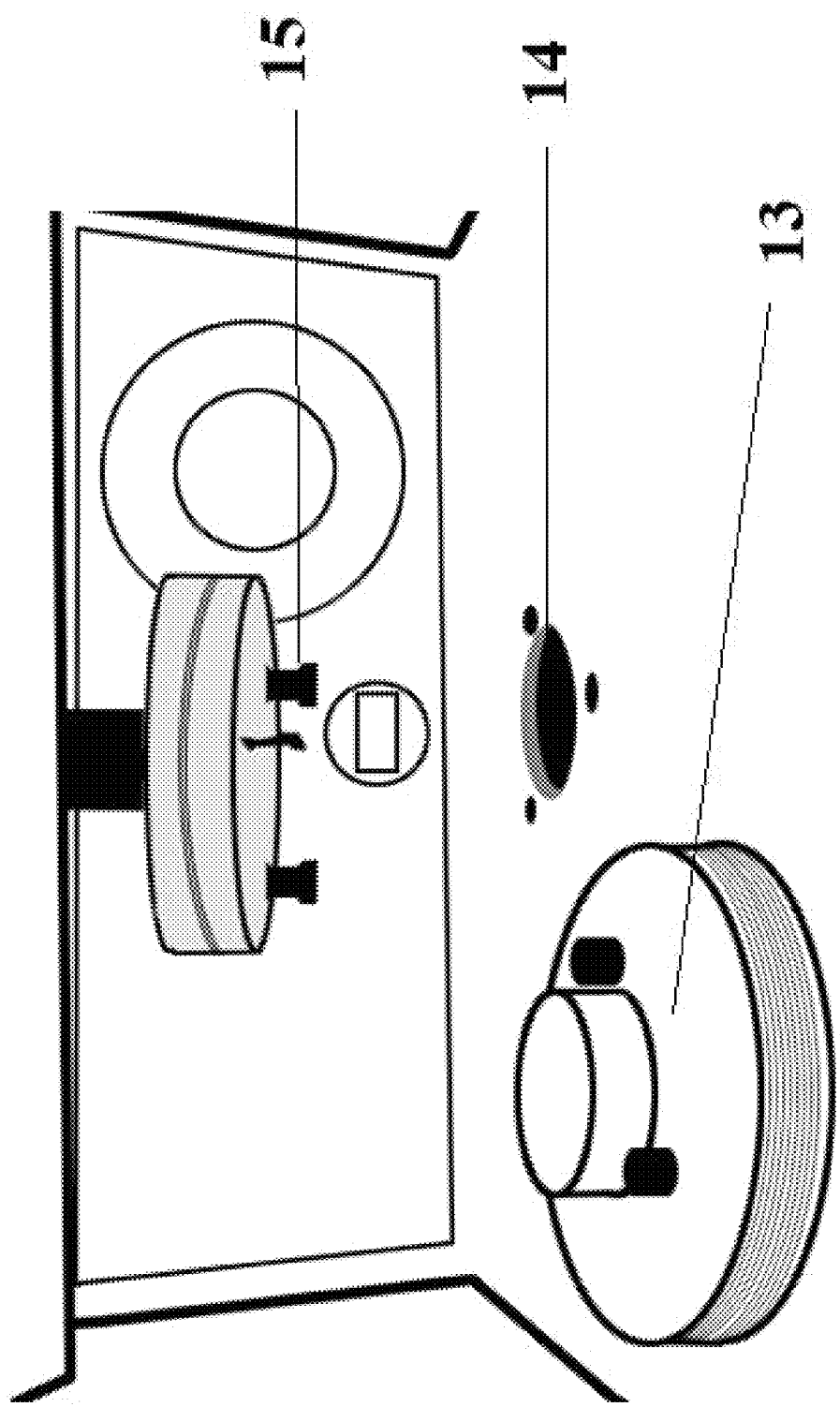
FIG. 9: The lower part of the sample holder that is placed in the slot and the part where it is placed in the instrument

In the device, a special sample holder (4) is used, which enables the measurement of samples having different thickness values (6,7). After the sample holder (4) is prepared outside the device by placing the sample (6,7) and the related parts, it is inserted in the insertion point of the device thus the load measurement sensors are prevented from being damaged due to overloading. The sample holder (4) can be easily moved outside the measurement area and inserted back. In order to be placed in the device, the back part (13) of the sample holder is placed on the insertion point (14) as shown in FIG. 9 and finally sample is ready for measurement.

Figure 6:
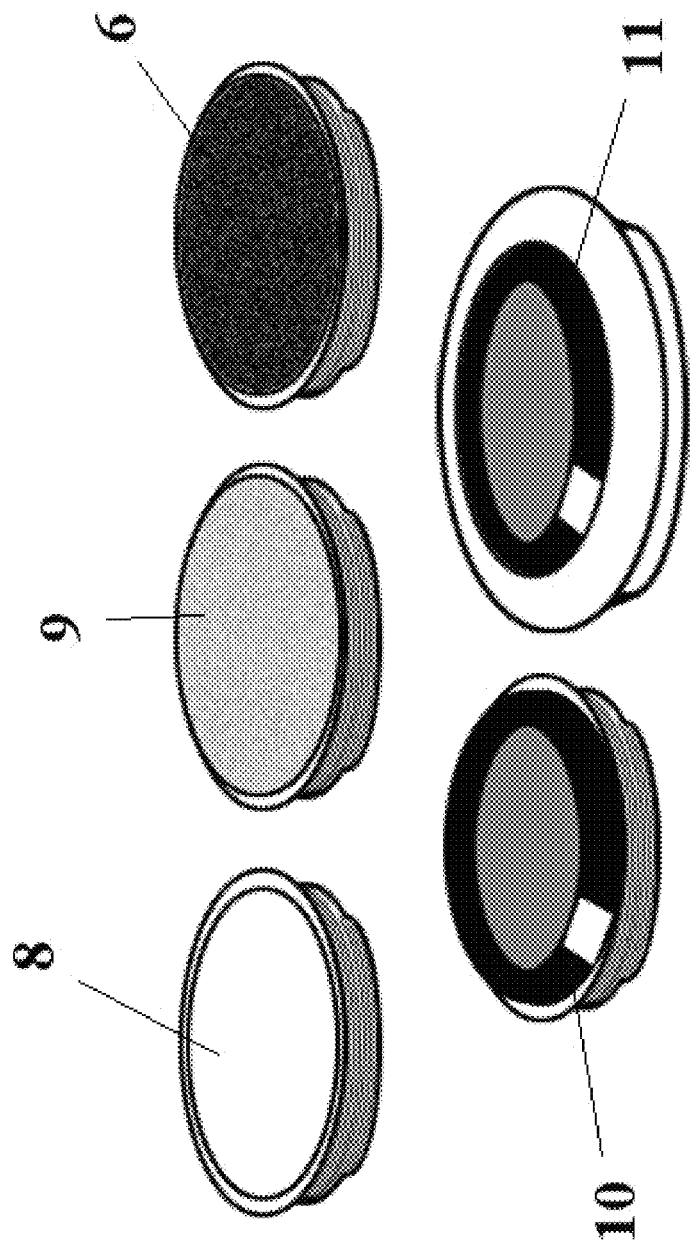
FIG. 6: Demonstration of sample placement in the sample holder in thick fabric samples
Figure 7:
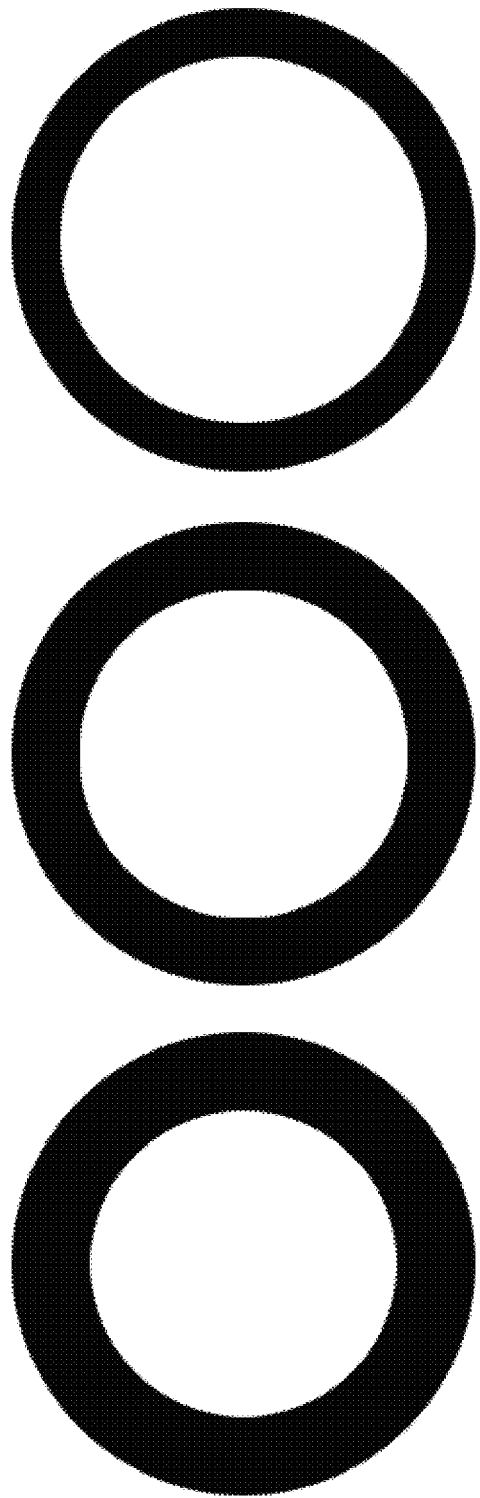
FIG. 7: Compression rings of different diameters

Placement of thick fabric samples (6) in the sample holder (4) is given in FIG. 6. First, the felt (9) is placed on the outer part of the sample holder (8). Thick fabric samples (6) are also covered on the felt (9) and compressed with the compression ring (10). Finally, the sample is ready for measurement after clamping it with the clamping ring (11). Normally during clamping the holders, surface deformations such as wrinkling may occur on the surface of the sample. In this invention compression rings with different inner diameters, changing between 55 and 65 mm, were designed to create a homogeneous pressure on the edges of the fabric and to prevent the occurrence of potting and/or wrinkling on the surface due to the movement made to clamp the ring (FIG. 7).

Figure 8:
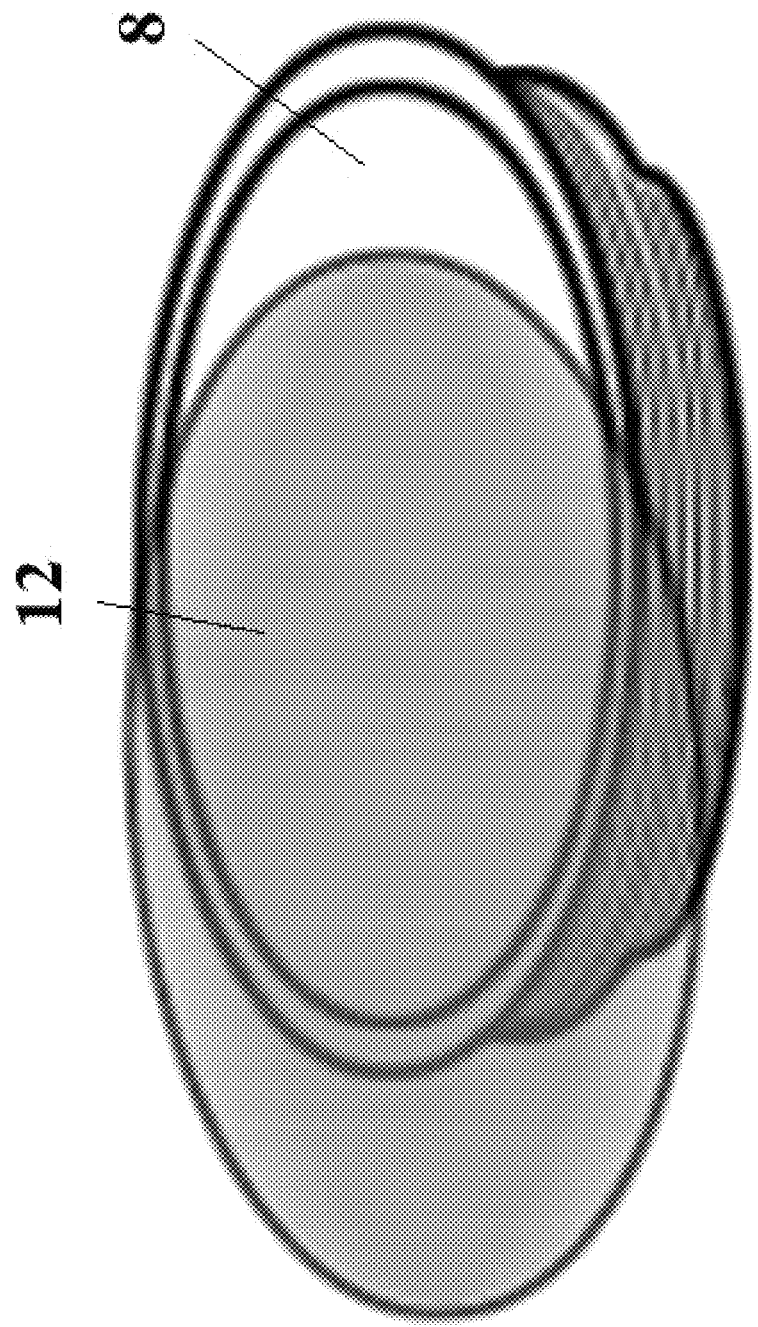
FIG. 8: Acrylic plate and placing acrylic plate on the outer part of sample holder

In thin fabric samples (7), a thin plate (12) is placed on the outer part (8) of the sample holder, since all other parts are placed on the thin plate (12), the thin fabric sample (7) is prevented from collapsing to the bottom part and forming a wrinkle on the surface (FIG. 8). When placing thick samples (6), there is no need to use this thin plate (12).

During the measurement, a light source (2) and camera system (3) are integrated on the device to allow the control of the amount of penetration of the nails through the fiber ends on the fabric surface. By means of this system, it is also possible to check the nail penetration before measurements.

Figure 12:
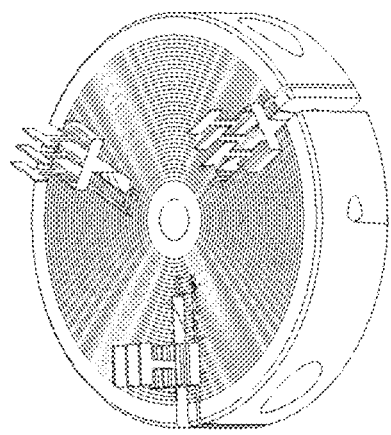
FIG. 12: View of 3 measurement heads with different number of nails (in the 2$^{nd}$ model measurement head)
Figure 12:
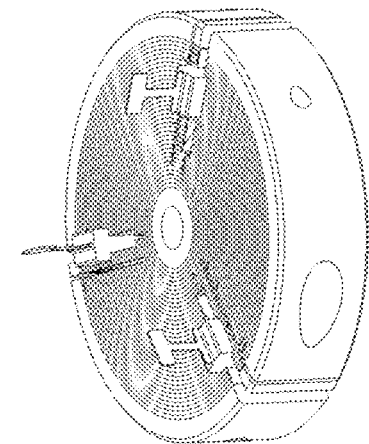
Figure 12:
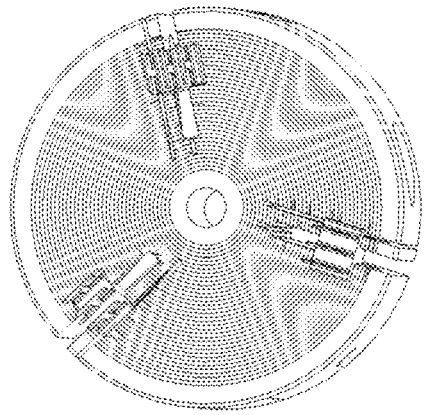

One of the different measuring heads (5) shown in FIG. 12 is attached to the part placed on the upper part of the measuring region before the measurement, depending on the type of fabric to be measured. Since the measuring head (5) is mounted on the upper part, the weight of the measuring head (5) has no effect on the measuring result, therefore, it is negligible.

Figure 10:
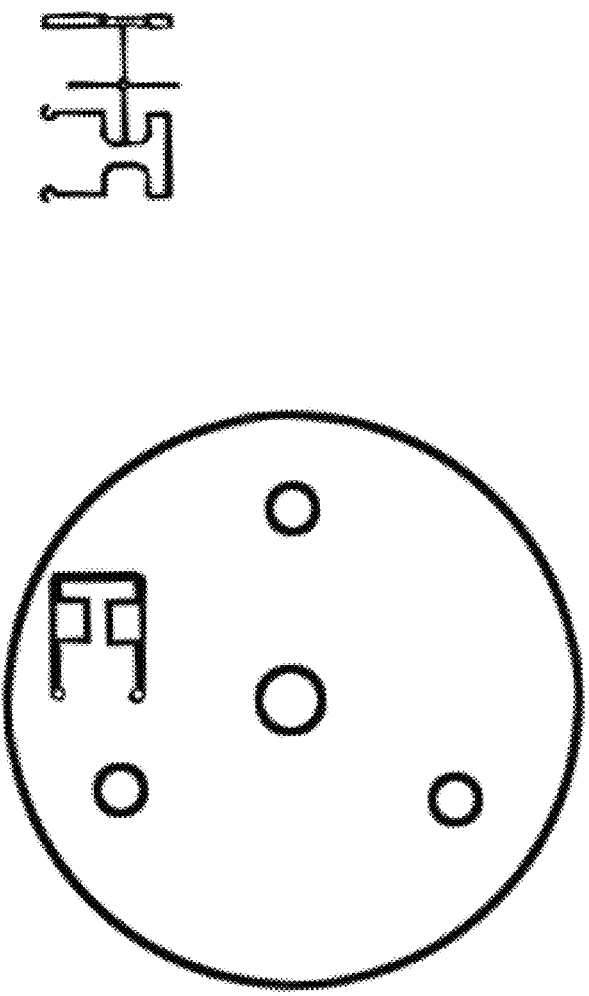
FIG. 10: The appearance of the structure forming the nail in the inner part of the measuring head (1$^{st}$ Model of Measurement head)
Figure 11:
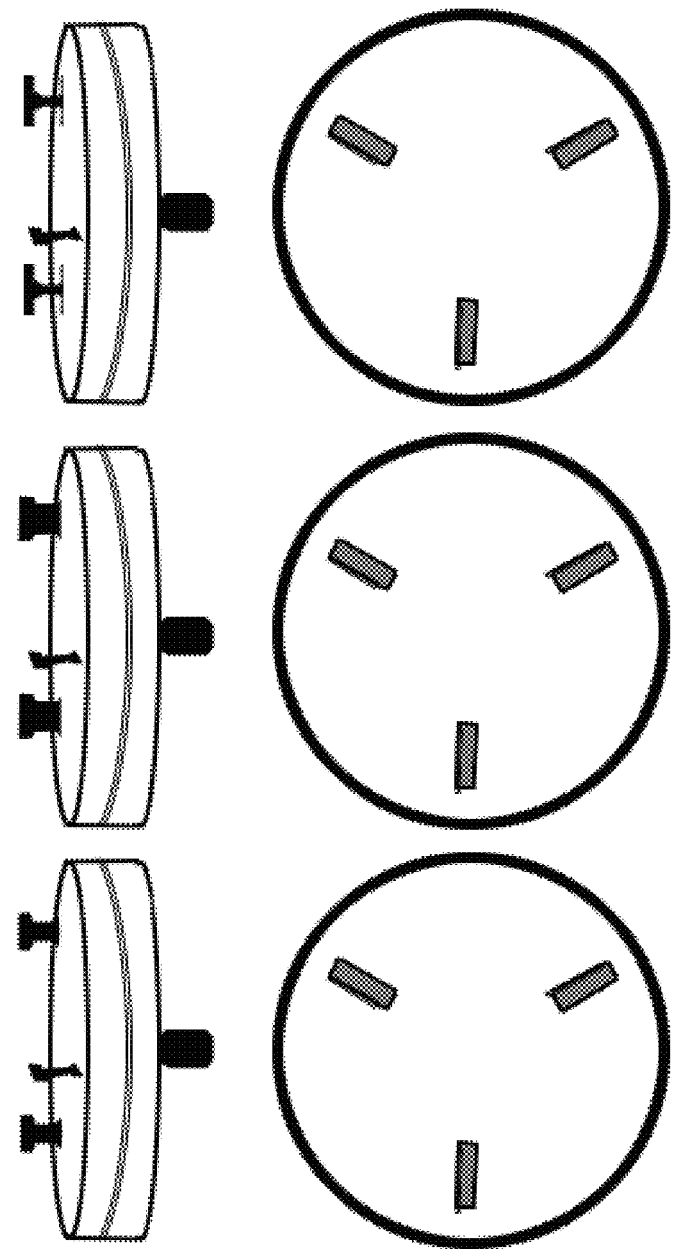
FIG. 11: Side and top views of 3 different measurement heads with 3 nails (in the 1$^{st}$ model)

Measuring heads (5) are available in two models. In the first model, the nail is on a surface and this surface is mounted on the inner side of the head, ensuring that the parts forming the nail (15) are outside the head and the measuring head is used in this integrated form. The structure of the nails (15) in this model is given in FIG. 10. The height and width of the nails (15) are designed to be adjusted as desired. There are 1-12 nails on the head and each nail have different width of neck parts. Nail height varies between 2-7 mm (FIG. 11).

In the second model, the blocks containing different shapes and numbers of nails are fixed by placing them in the sections allocated to the fixed measuring head, and this combined measuring head structure is used by mounting it on the device. Examples of measurement heads with different numbers of nails are given in FIG. 12.

The heads (5) are magnetically mounted on the upper part of the measurement zone and fixed before the measurement. Then the measurement is started, after pressing the "start" button in the computer software that is specially designed for the device.

During the measurement, the effect created by the friction force caused by the contact of the nails with the fiber ends and the vibration due to force fluctuation can be followed from the torq change curve on the screen. In order to enter other physical properties of the fabric, special areas are reserved in the program. The results can be taken in excel file format and automatically recorded by the device on the date of the test.

There are various measurement heads consisting different number of nails which also can be in different shapes. To place the nails on the gaps in the measurement heads, it is sufficient to tighten that area with a screw. Different design head productions were carried out to tighten the region where the nails will be placed on the header. The views of the produced measurement heads are given in FIG. 13 and FIG. 14.

Figure 14:
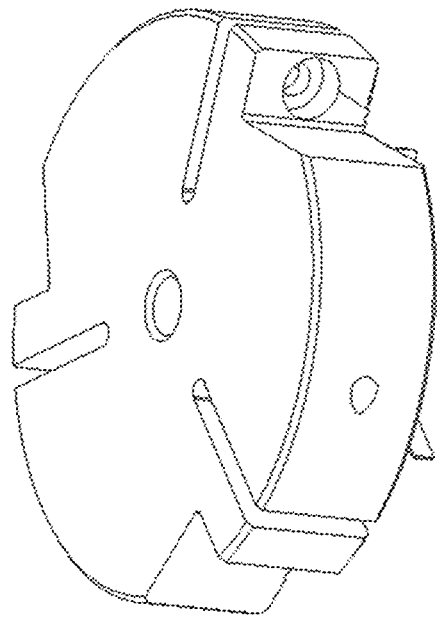
FIG. 14: View of the measurement head 2
Figure 13:
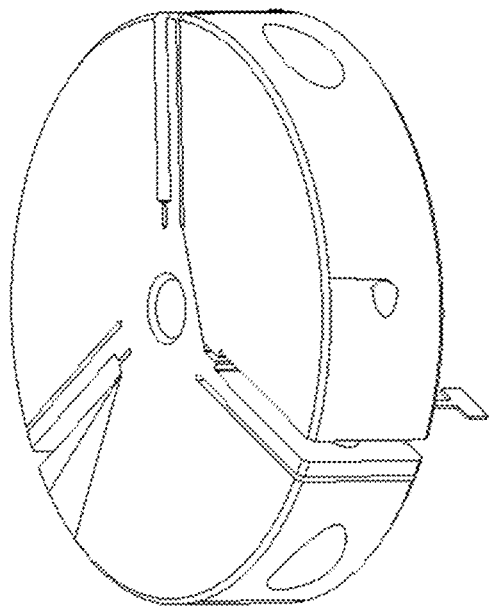
FIG. 13: View of the measurement head 1
Figure 15:
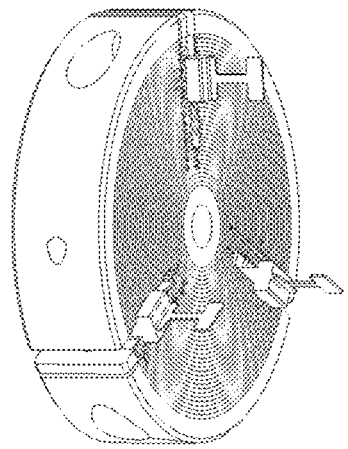
FIG. 15-18: Measuring heads ready for measurement by placing different numbers of nails on the measurement head 13
Figure 16:
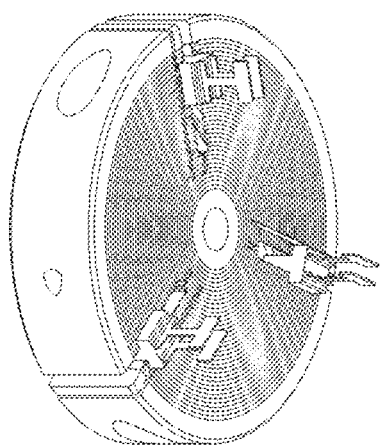
Figure 17:
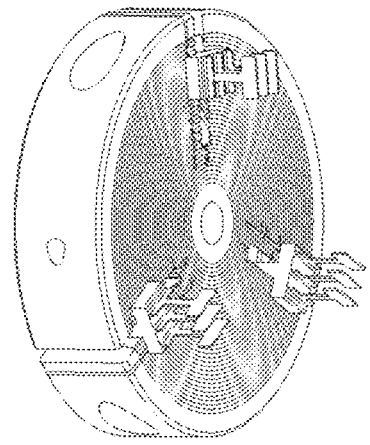
Figure 18:
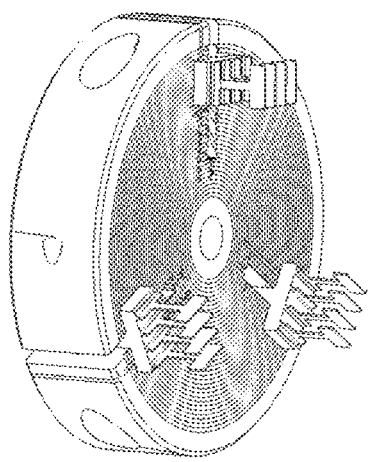
Figure 20:
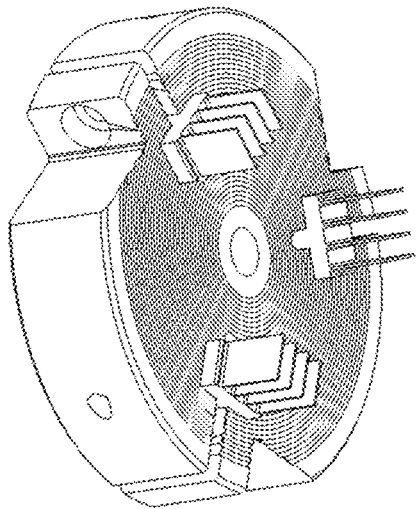
FIG. 19-21: Measuring heads ready for measurement by placing different numbers of nails on the measurement head 14
Figure 19:
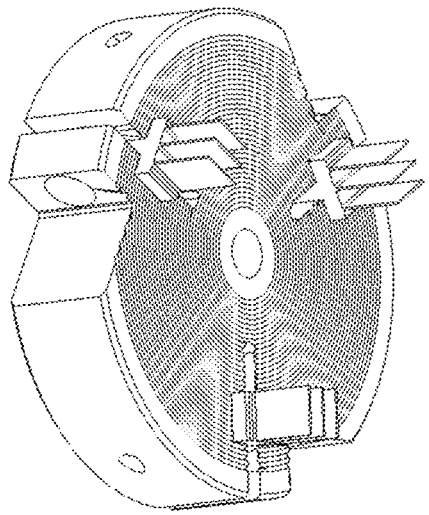
Figure 21:
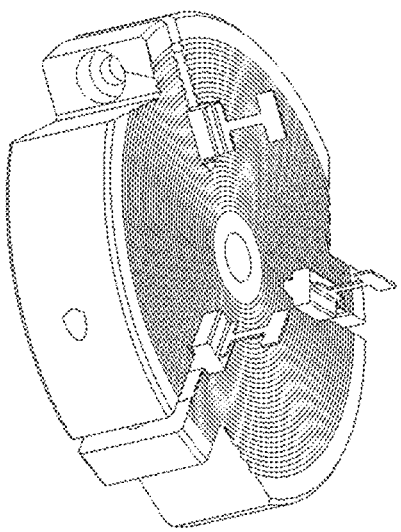
Figure 22:
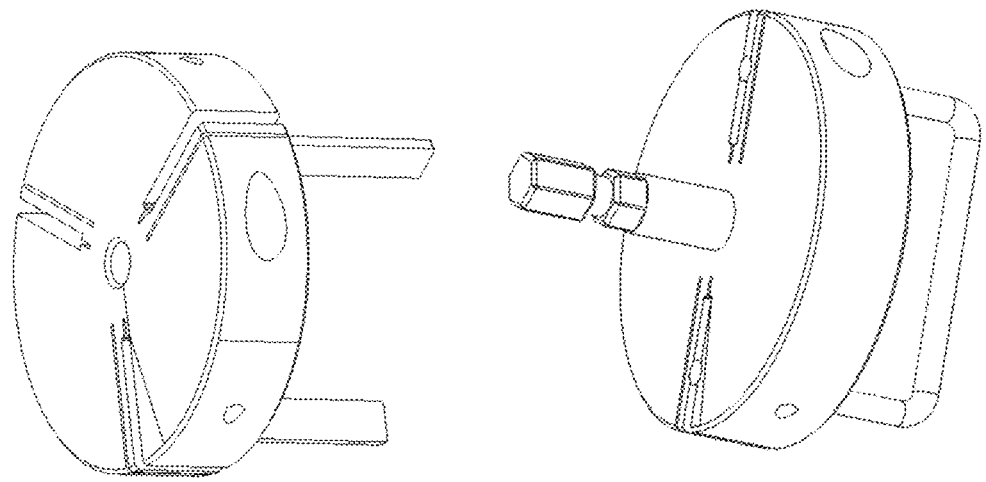
FIG. 22: Measuring heads for determination of roughness and prickle of the labels.
Figure 22:
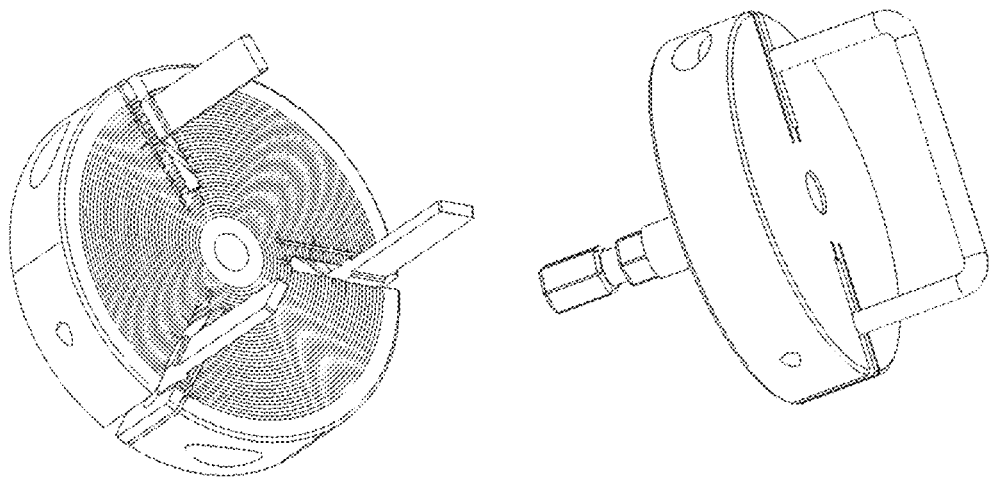

The measurement heads, prepared by placing different number of nails in the head that is given in FIG. 13, are given in FIG. 15-18. Similarly measuring heads, prepared by placing different numbers of nails in the head that is given in FIG. 14, are given in FIG. 19-21. FIG. 22 indicates the design of measurement head to be used for the determination of roughness of different types of fabrics. The measurement head suggested for determining prickle of the labels in the clothes is also-showed in FIG. 22.

REFERENCES

Research Center of Hunan Ramie Technology. 1997. "The Evaluation Method of Prickle Sensation Caused by Wearing Ramie Garment", J. Linen Textile Technology, 20, 31-34.
James Ramsay Donald. 2012. Patent NZ593817 (A)—Apparatus for measuring the fibre prickle of a fabric, comprising a string in a mounting means that is moved across a surface of the fabric, wherein protruding fibre ends engage the string and a sensor measures the vibration in the string.
Patent ZL200420019685.6—One-side Fabric Compressing Tester
Ramsay, D. J., Fox D. B., Naylor G. R. S. 2012. "An Instrument for Assessing Fabric Prickle Propensity", Textile Research Journal, 82, 513-520.
Wool Comfort and Handle, http://www.woolcomfortandhandle.com/index.php/wool-comfortmeter, Son erişim tarihi: Oct. 10, 2018.
Tester, Naebe, M., McGregor B. A., Swan P., Tester D. 2014. "Associations between the Physiological Basis of Fabric-Evoked Prickle, Fiber and Yarn Characteristics and the Wool ComfortMeter Value", Textile Research Journal, 0(00), 1-9.
D. H. 2010. "Relationship between Comfort Meter Values and the Prickle Rating of Garments in Wearer Trials", Animal Production Science, 50, 1077-1081.
Naebe, M., McGregor B. A., Swan P., Tester D. 2014. "Associations between the Physiological Basis of Fabric-Evoked Prickle, Fiber and Yarn Characteristics and the Wool ComfortMeter Value", Textile Research Journal, 0(00), 1-9.
Ao, L., Tang W., Yang Y., Yu C. 2007. "The Analyzing and Simulating of the Interaction Between Skin and Fabric", Proceedings of the Sixth International Conference on Machine Learning and Cybernetics, 19-22 Aug. 2007, Hong Kong.
Hu, J. 2006. Characterization of Sensory Comfort of Apparel Products, Ph.D. Thesis, Institute of Textiles and Clothing, The Hong Kong Polytechnic University.
Süpüren Mengüç G., Özdil N, Hes L. 2015. "Prickle and Handle Properties of Fabrics Produced from Specialty Animal Fibers", Textile Research Journal, 0(00), 1-13, DOI: 10.1177/0040517515578327.
Bozdoğan, F. 2009. Fiziksel Tekstil Muayeneleri (Kumaş Testleri), İzmir: E. Ü. Tekstil ye Konfeksiyon Araştırma Uygulama Merkezi Yayınları.
James Ramsay Donald. 2012. Patent NZ593817 (A)—Apparatus for measuring the fibre prickle of a fabric, comprising a string in a mounting means that is moved across a surface of the fabric, wherein protruding fibre ends engage the string and a sensor measures the vibration in the string.
Süpüren Mengüç, G. 2012. Bazi Özel Hayvansal Liflerden Elde Edilen İpliklerden Üretilen Kumaşlarin Özellikleri Üzerine Bir Araştırma, Ege Üniversitesi Fen Bilimleri Enstitüsü, Doktora Tezi, İzmir.
Li, T., Shao J., Zhou J., Zhang T. 2012. "The Evaluation of Fabric Prickle Based on BP Neural Network", Advanced Materials Research, 441, 645-650.
CSIRO Division of Wool Technology. 1988. "Prickle and Its Prevention", Textile Asia, 19(5), 95-99.
Naylor, G. R. S., Veitch C. J., Mayfield R. J. 1992. "Fabric-Evoked Prickle", Textile Research Journal, 62(8), 487-493.
James Ramsay Donald. 2012. Patent NZ593817 (A)—Apparatus for measuring the fibre prickle of a fabric, comprising a string in a mounting means that is moved across a surface of the fabric, wherein protruding fibre ends engage the string and a sensor measures the vibration in the string

What is claimed is:

1. A test method for determining a prickle property of fabrics objectively, comprising performing a measurement with a circular friction force motion, wherein for a measurement of a thick fabric sample, the test method further comprises the following steps: placing a felt on an outside of a sample holder, covering the thick fabric sample on the felt, compressing with a compression ring, and finally with a clamping ring, clamping the thick fabric sample and fixing the thick fabric sample.

* * * * *